United States Patent [19]

Nichols et al.

[11] Patent Number: 5,493,027

[45] Date of Patent: Feb. 20, 1996

[54] ANTICONVULSIVE AGENTS AND USES THEREOF

[75] Inventors: Alfred C. Nichols, San Jose; K. Lemone Yielding, Galveston, both of Tex.

[73] Assignee: Board of Regents, the University of Texas System, Austin, Tex.

[21] Appl. No.: 6,918

[22] Filed: Jan. 22, 1993

[51] Int. Cl.$^6$ ............................ C07D 215/18; C07D 215/46
[52] U.S. Cl. .............................................. 546/156; 546/159
[58] Field of Search .................................. 546/156, 159; 514/312, 313

[56] References Cited

U.S. PATENT DOCUMENTS

| | | | |
|---|---|---|---|
| 4,788,188 | 11/1988 | Verniere et al. | 514/212 |
| 4,789,678 | 12/1988 | Effland et al. | 514/313 |
| 4,806,550 | 2/1989 | Ife et al. | 514/313 |
| 4,840,942 | 6/1989 | Effland et al. | 514/313 |
| 5,006,535 | 4/1991 | Ife et al. | 514/313 |
| 5,017,576 | 5/1991 | Dubroeucq et al. | 514/228.2 |
| 5,026,700 | 6/1991 | Harrison et al. | 514/233.8 |
| 5,028,707 | 7/1991 | Nichols et al. | 546/156 |
| 5,102,892 | 4/1992 | Geiss et al. | 514/313 |
| 5,250,541 | 10/1993 | Moroni et al. | 514/312 |

FOREIGN PATENT DOCUMENTS

PCT/US94/00128 5/1994 WIPO.

OTHER PUBLICATIONS

Harrison, et al., *J. Med. Chem.*, vol. 33, pp. 3130–3132 (1990).

Baron et al., "Activity of 5,7–Dichlorokynurenic Acid, a Potent Antagonist at the N–Methyl–D–aspartate Receptor–Associated Glycine Binding Site," *Molecular Pharmacology*, 38:554–561, 1990, published in USA.

Collingridge et al., "NMDA Receptors—Their Role in Long–Term Potentiation," *TINS*, 10(7):288–293, 1987, published in UK.

Cortes et al., "Effect of Structural Modification of the Hydrantoin Ring on Anticonvulsant Activity," *J. Med. Chem.*, 28:601–606, 1985, published in USA.

Dingledine et al., "Excitatory Amino Acid Receptors in Epilepsy," *TIPS*, 11:334–338, 1990, published in Europe.

Foster et al., "Kynurenic Acid Analogues with Improved Affinity and Selectivity for the Glycine Site on the N–Methyl–D–aspartate Receptor from Rat Brain," *Molecular Pharmacology*, 41:914–922, 1992, published in USA.

Giulian et al., "Secretion of Neurotoxins by Mononuclear Phagocytes Infected with HIV–1," *Science*, 250:1593–1596, 1990, published in USA.

Goehring et al., "Synthesis and Anticonvulsant Activity of 2–Benzylglutarimides," *J. Med. Chem.*, 33:926–931, 1990, published in USA.

Greenamyre & Young, "Excitatory Amino Acids and Alzheimer's Disease," *Neurobiology of Aging*, 10:593–602, 1989, published in USA.

Harrison et al., "4–[(Carboxymethyl)oxy]– and 4–[(Carboxymethyl)amino]–5, 7–dichloroquinoline–2–carboxylic Acid: New Antagonists of the Strychnine–Insensitive Glycine Binding Site on the N–Methyl–D–aspartate Receptor Complex," *J. Med. Chem.*, 33:3130–3132, 1990, published in USA.

Heindel et al., "Cyclization of Aniline–Acetylenedicarboxylate Adducts. A Modified Conrad–Limpach Method for the Synthesis of Potential Antimalarials," *J. Med. Chem.*, 11:1218–1221, 1968, published in USA.

Huettner, J. E., "Indole–2–Carboxylic Acid: A Competitive Antagonist of Potentiation by Glycine at the NMDA Receptor," *Science*, 243:1611–1613, 1989, published in USA.

Huettner, J. E., "Competitive Antagonism of Glycine at the N–Methyl–D–Aspartate (NMDA) Receptor," *Biochemical Pharmacology*, 41(1):9–16, 1991, published in Europe.

Izumi et al., "Quisqualate and N–methyl–D–aspartate (NMDA) Receptors in Induction of Hippocampal Long–Term Facilitation Using Conditioning Solution," *Neuroscience Letters*, 83:201–206, 1987, published in Europe.

Johnson & Ascher, "Glycine Potentiates the NMDA Response in Cultured Mouse Brain Neurons," *Nature*, 325:529–531, 1987, published in UK.

Jones et al., "Characterization of the Binding of Radioligands to the N–Methyl–D–Aspartate, Phencyclidine, and Glycine Receptors in Buffy Coat Membranes," *Journal of Pharmacological Methods*, 21:161–168, 1989, published in USA.

Kemp et al., "7–Chlorokynurenic Acid is a Selective Antagonist at the Glycine Modulatory Site of the N–methyl–D–aspartate Receptor Complex," *Proc. Natl. Acad. Sci. USA*, 85:6547–6550, 1988, published in USA.

Kleckner & Dingledine, "Selectivity of Quinoxalines and Kyurenines as Antagonists of the Glycine Site on N–Methyl–D–aspartate Receptors," *Molecular Pharmacology*, 36:430–436, 1989, published in USA.

McBain et al., "Structural Requirements for Activation of the Glycine Coagonist Site of N–Methyl–D–aspartate Receptors Expressed in Xenopus Oocytes," *Molecular Pharmacology*, 36:556–565, 1989, published in USA.

Morris et al., "Selective Impairment of Learning and Blockage of Long–Term Potentiation by an N–methyl–D–aspartate Receptor Antagonist, AP5," *Nature*, 1986, 319:774–776, published in Europe.

Nichols and Yielding, "Anticonvulsive Activity of Antagonists at the Glycine Modulatory Site on the NMDA Receptor Complex," *Society for Neuroscience*, Abstract #497.2, p. 1255, Nov., 1991, place of place of publication unknown.

Nowak et al., "Magnesium Gates Glutamate–Activated Channels in Mouse Central Neurones," *Nature*, 1984, 307:462–465, published in Europe.

Rondouin et al., "Non–competitive Antagonists of N–methyl–D–aspartate Receptors Protect Cortical and Hippocampal Cell Cultures Against Glutamate Neurotoxicity," *Neuroscience Letters*, 1988, 91:199–203, published in Europe.

Rothman, S., "Synaptic Release of Excitatory Amino Acid Neurotransmitter Mediates Anoxic Neuronal Death," *The Journal for Neuroscience*, 1984, 4(7):1884–1891, published in USA.

Singh et al., "Modulation of Seizure Susceptibility in the Mouse by the Strychnine–Insensitive Glycine Recognition Site of the NMDA Receptor/Ion Channel Complex," *British J. of Pharmacology*, 1990, 99:285–288, published in Europe.

Snell & Johnson, "Characterization of the Inhibition of Excitatory Amino Acid–Induced Neurotransmitter Release in the Rat Striatum by Phencyclidine–Like Drugs," *The Journal of Pharmacology and Experimental Therapeutics*, 238(3):938–946, published in USA, 1986.

Spencer et al., "Guam Amyotrophic Lateral Sclerosis–Parkinsonism–Dementia Linked to a Plant Excitant Neurotoxin," *Science*, 1987, 237:517–522, published in USA.

Stone & Perkins, "Quinolinic Acid: A Potent Endogenous Excitant at Amino Acid Receptors in CNS," *European Journal of Pharmacology*, 72:411–412, 1981, published in Europe.

Surrey & Hammer, "Some 7–Substituted 4–Aminoquinoline Derivatives," *J. Am. Chem. Soc.*, 68:113–116, 1946, published in USA.

Swinyard & Kupferberg, "Antiepileptic Drugs: Detection, Quantification, and Evaluation," *Federation Proceedings*, 44(10):2629–2633, 1985, published in USA.

Tucker et al., "Apparent Ionization Exponents of 4–Hydroxyquinoline, 4–Methoxyquinoline and N–Methyl–4–quinolone; Evaluation of Lactam–Lactim Tautomerism," *J. Am. Chem. Soc.*, 73:1923–1928, 1951, published in USA.

Vida & Gerry, "Anticonvulsants," *Academic Press*, N.Y., N.Y., pp. 176–183, 1977, published in USA.

Watkins et al., "Structure–Activity Relationship in the Development of Excitatory Amino Acid Receptor Agonists and Competitive Antagonists," *Trends in Pharmacological Sciences*, 11:25–33, 1990, published in Europe.

White et al., "Glycine Binding to Rat Cortex and Spinal Cord: Binding Characteristics and Pharmacology Reveal Distinct Populations of Sites", *Journal of Neurochemistry*, 53(2):503–512, 1989, published in USA.

Wong et al., "The Anticonvulsant MK–801 is a Potent N–methyl–D–aspartate Antagonist," *Proc. Natl. Acad. Sci. USA, 83:7104–7108, 1986, published in USA.

Wright, R. Gordon, "A Simple One–Pot Conversion of Alkyl 4–Oxo–1,4–dihydroquinoline–2–carboxylates to 4–Aminoquinoline–2–carboxylates using Reactive Isocyanates," *Synthesis*, 1058–1061, 1984, published in Europe.

Young et al., "NMDA Receptor Losses in Putamen from Patients with Huntington's Disease," *Science*, 241:981–983, 1988, published in USA.

Dialog Search, 1992, printed in USA.

Johnson & Ascher, "Glycine Potentiates the NMDA Response in Cultured Mouse Brain Neurons," *Nature*, 325:529–531, 1987, published in Europe.

Porter et al., "Antiepileptic Drug Development Program," *Cleveland Clinic Quarterly*, 51(2):293–305, 1984, published in USA.

Rogawski & Porter, "Antiepileptic Drugs: Pharmacological Mechanisms and Clinical Efficacy with Consideration of Promising Developmental Stage Compounds," *Pharmacological Reviews*, 42(3):223–286, 1990, published in USA.

Snell, "The Allosteric Interactions between the N–methyl–D–aspartate (NMDA) and Glycine Sites of the NMDA Receptor/Ionophore Complex, A Dissertation", The University of Texas Medical Branch, Galveston, Texas, 1990, published in USA.

*Primary Examiner*—Alan L. Rothman
*Assistant Examiner*—D. Margaret M. Mach
*Attorney, Agent, or Firm*—Arnold, White & Durkee

[57] ABSTRACT

Coupled to the N-methyl-D-aspartate (NMDA) receptor-channel complex is a strychnine-insensitive binding site for glycine. Pharmacological antagonism of glycine binding at this site can produce anticonvulsant activity. Derivatives of kynurenic acid, pyridine and 2-carboxy-indole were synthesized and evaluated as antagonists of glycine binding and for anticonvulsant effects. Compounds were tested in mice against seizures induced by electroshock and pentylenetetrazole, and in the rotorod assay for neurologic deficit. The derivatives were also assayed for binding at the NMDA-associated glycine site. The most potent anticonvulsant was ethyl 4-methylamino-5,7-dichloro-2-quinoline carboxylate. This compound provided protection against maximal electroshock (MES) induced seizures at a dose of 30 mg/kg. Other compounds were active at 100 mg/kg dose level, including 5-fluoro-2-indole carboxylic acid and the diethyl ester of 2,6-pyridine dicarboxylic acid.

2 Claims, 3 Drawing Sheets

FIG. 1

7-Chloro-Kynurenic Acid

FIG. 2

5-Fluoro-Indole-2 Ethyl Carboxylate

FIG. 3

2, 6-Pyridine-Di(Ethyl Carboxylate)

ANTICONVULSIVE AGENTS AND USES THEREOF

BACKGROUND OF THE INVENTION

The present invention relates to a agents useful as excitatory amino acid antagonists. The quinoline and kynurenin derivatives of the present invention have affinity for the glycine binding site of the NMDA receptor. Compounds of the present invention should be usable for the treatment of epilepsy, treatment of neurodegenerative diseases, prevention of eschemic/hypoxic damage to cerebral tissue or other syndromes involving inhibition or excessive stimulation of the NMDA receptor complex.

There is an increasing body of evidence that excitatory amino acid neurotransmitter systems are progressively affected in the course of Alzheimer's disease (AD) (Greenamyre, et al.; Foster et al., Penney et al.). Excitatory amino acid neurotransmitter systems are important in memory and learning (Izumi et al.; Morris et al.), and have been implicated in a number of CNS disorders including epilepsy (Wong et al.), hypoxia/ischemia brain damage (Rothman), Huntington's disease (Young et al.), AIDS encephalopathy (Giulian et al.), and amyotrophic lateral sclerosis (Spencer et al.). A specific set of these excitatory receptors are of particular interest, those that selectively bind N-methyl-D-aspartic acid (NMDA). Activation of this transmitter system is probably a necessary early step in the formation of certain types of memory (Collingridge et al.), yet over-stimulation of these receptors can be toxic and result in cell death (Rondouin et al.). It should be feasible to design and synthesize efficacious amino acid analogs as therapeutic agents for this receptor, once binding characteristics are understood. However, it needs to be remembered that a direct agonist for the NMDA receptor could be neurotoxic, while an antagonist might potentiate memory loss. Research relating to the present application has been directed towards the glycine modulatory site on the NMDA receptor complex (Johnson et al.). Development of a strategy for pharmacological intervention at this site should lead to the production of drugs with mixed agonist-antagonist activities such that they are clinically useful while having minimal side effects.

The NMDA-sensitive receptor sites comprise a subset of the excitatory neuroreceptors that are activated by L-glutamic acid. This particular type of receptor is coupled to an ion channel which is voltage dependent and permeable to calcium. The receptor complex also has a strychnine-insensitive binding site for glycine. Occupation of this glycine site is thought necessary to produce channel opening. There is evidence that NMDA receptors are responsible, at least in part, for the neurotoxicity seen in ischemia, and to excitatoxic cell death (Rondouin et al.). Excitotoxicity is the neuronal degeneration caused by exposure of CNS tissue to excitatory amino acids. It has been shown that non-competitive antagonists of NMDA receptors protect cortical and hippocampal cell cultures against glutamate neurotoxicity (Rondouin et al.). Calcium entry through the NMDA receptor channel is thought to be the mechanism by which glutamate released from nerve terminals can regulate long-term physiological events and, under pathological conditions, precipitate neurodegeneration.

As used in the present application: the term "halogen" refers to fluorine, chlorine or bromine; the term "lower alkyl group", refers to a branched or straight-chained alkyl group containing from 1 to 6 carbon atoms; the term "pharmaceutically acceptable addition salt" applies to any nontoxic organic or inorganic addition salt of the basic compounds described herein. These may be acid addition salts or basic addition salts. Typical inorganic acid addition salts include those resulting from hydrochloric, hydrobromic, sulfuric, phosphoric and acid methyl salts such as sodium monohydrogen, orthophosphate and potassium hydrogen sulfate. Illustrative organic acids which form acceptable salts include mono-, di- and tricarboxyllic acids, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, and so forth. Pharmaceutically acceptable basic addition salts applied to any organic or inorganic basic addition salts including those resulting from alkali metal or alkali-earth metal hydroxides, ammonia, aliphatic, alicyclic or aromatic organic amines.

Epilepsy is a complex disease process with many possible etiologies. This is reflected in the variety of chemicals which have been used therapeutically to treat seizures. Yet some 20–40% of epileptic patients fail to experience satisfactory seizure control with the drugs currently available (Goehring et al., 1990). An antiepileptic compound can affect either the initiation of the epileptic discharge or its spread within the brain. In either case, the drug ultimately must attenuate neuronal excitability. This can be accomplished by at least three different mechanisms: modulation of voltage-dependent ion channels, enhancement of CNS inhibitory pathways, or suppression of excitatory pathways (Rogawski, et al. 1990). An ideal drug should act specifically at the site of inappropriate excitation, rather than broadly inhibiting neuronal activity. In this manner, untoward side effects such as ataxia and sedation can be minimized. Pathways utilizing the excitatory neurotransmitter L-glutamic acid offer several potential targets for therapeutic intervention. Since neuroreceptors for this amino acid transmitter exist as several pharmacologically different subtypes (Watkins et al., 1990), therapeutic agents can be selected on the basis of binding specificity for a given receptor subset.

The N-methyl-D-aspartate (NMDA) activated subset of neuroreceptors for L-glutamate is linked to a nonselective cation channel (Nowak et al., 1984). For channel opening to occur, however, a strychnine-insensitive glycine binding site on the receptor-channel complex must be occupied (Johnson and Ascher, 1987). Antagonism of glycine binding at this site inhibits NMDA responses (Kemp et al., 1988). Also located on this receptor-channel complex is a binding site for the dissociative anesthetic phencyclidine. Occupation of this site also blocks NMDA-mediated responses in a noncompetitive manner (Snell and Johnson, 1986). Since glutamate functions as an excitatory neurotransmitter, it is not surprising that competitive inhibitors of NMDA activity have been shown to have anticonvulsant properties (Dingledine et al., 1990). Chemicals which noncompetitively antagonize NMDA activity by binding either at the phencyclidine site (such as MK-801) or at the glycine site (7-chlorokynurenic acid) likewise demonstrate anticonvulsant activity (Wong et al., 1986; Singh, et al., 1990).

The glycine binding site on the NMDA receptor complex presents a unique target for treatment of seizures arising in NMDA activated neurons. Chemical analogs of excitatory amino acid transmitters usually are ionized at physiological pH. Consequently, they are best applied directly into the CNS, as charged molecules often have difficulty crossing the blood-brain barrier. This limits their usefulness as therapeutic agents. Two different groups of aromatic chemicals have been reported to interact at the NMDA-associated glycine site: kynurenic acids (4-hydroxy-2-quinolinecarboxylic acid) (Kemp, et al., 1988) and indole-2-carboxylic acids (Huettner, 1989). Derivatives lipophilic enough to pass from the systemic circulation into the CNS can be produced from each of these groups. Through the use of ligands for the glycine site, NMDA receptor activity can be modulated without interfering with other excitatory transmission pathways. Furthermore, binding characteristics of the NMDA-associated glycine sites are distinct from those of the inhibitory (strychnine-sensitive) glycine receptors in the spinal cord, with both kynurenate (kyn) (White, et al, 1989) and indole-2-carboxylic acid (Huettner, 1989) being inactive at the strychnine-sensitive sites.

The present invention involves, in one aspect, a series of kynurenic acid derivatives and indole esters as well as the anticonvulsant potential of these compounds and their potencies as glycine inhibitors. Also tested were pyridine-2,6-dicarboxylic acid and its corresponding diethyl ester, based on structural similarity to kynurenic acid and a report by Stone and Perkins (1981) that 2,3-pyridine dicarboxylic acid acts on NMDA neurons. Anticonvulsant evaluation was conducted against both maximal electroshock (MES) and maximal electroshock induced seizures (Swinyard and Kupferberg, 1985; Porter, et al., 1984). Rotorod testing was used to determine if the compounds caused a neurological deficit. A synaptosomal assay was utilized to determine strychnine-insensitive glycine binding inhibition (Jones, et al., 1989).

SUMMARY OF THE INVENTION

Coupled to the N-methyl-D-aspartate (NMDA) receptor-channel complex is a strychnine-insensitive binding site for glycine. Pharmacological antagonism of glycine binding at this site can produce anticonvulsant activity. Derivatives of kynurenic acid, pyridine and 2-carboxy-indole were synthesized and evaluated as antagonists of glycine binding and for anticonvulsant effects. Compounds were tested in mice against seizures induced by electroshock and pentylenetetrazole, and in the rotorod assay for neurologic deficit. The derivatives were also assayed for binding at the NMDA-associated glycine site. The most potent anticonvulsant was ethyl 4-methylamino-5,7-dichloro-2-quinoline carboxylate. This compound provided protection against maximal electroshock (MES) induced seizures at a dose of 30 mg/kg. Other compounds were active at 100 mg/kg dose level, including 5-fluoro-2-indole carboxylic acid and the diethyl ester of 2,6-pyridine dicarboxylic acid.

An important embodiment of the present invention involves an anticonvulsive compound having the structure:

where $R^1$ is H or absent; $R^2$ is H, $CH_3$, $C_2H_5$ or $C_3H_7$; $R^3$ is H; $R^4$ and $R^{4a}$ are independently H, $CH_3$, $C_2H_5$ or $C_3H^5$; $R^5$ is H, F or Cl; $R^6$ is H; $R^7$ is F or Cl; $R^8$ is H or $CH_3$; and X is O or NH with the provisos that when $R^2$ is $CH_3$, $R^4$ and $R^{4a}$ are H; when $R^2$ is H, $R^4$ is $CH_3$. This structure of course includes any pharmaceutically acceptable addition salts well known to those of skill in the art.

In a more preferable aspect the present invention involves an anticonvulsive compound having the above structure:

where: $R^1$ is absent; $R^2$ is H, $CH_3$ or $C_2H_5$; $R^3$ is H; $R^4$ is H or $CH_3$, $R^{4a}$ is H; $R^5$ is Cl; $R^6$ is H; $R^7$ is Cl; $R^8$ is H; and X is O; with the proviso that: when $R^2$ is $CH_3$, $R^4$ and $R^{4a}$ are H; and when $R^2$ is H, $R^4$ is $CH_3$ and $R^{4a}$ is H.

Preferred embodiments of the present invention include a compound having the above structure where $R^2$ is $C_2H_5$. Another preferred embodiment includes a compound of the above structure where $R^4$ is $CH_3$.

Yet another preferred embodiment of the present invention includes a compound having the above structure where X is O, $R^8$ is H, $R^2$ is $C_2H_5$, $R^4$ is $CH_3$, and $R^5$ and $R^7$ are Cl. $R^5$ and $R^7$ may be F in place of Cl.

Another preferred embodiment of the present invention is an anticonvulsive compound having the above structure where $R^4$ and $R^8$ are H, $R^2$ is $CH_3$ and $R^5$ and $R^7$ are Cl. And still another preferred embodiment of the present invention includes an anticonvulsive compound of the same structure where $R^2$ and $R^8$ are H, $R^4$ is $CH_3$ and $R^5$ and $R^7$ are Cl. Convulsions may be prevented or treated by administering therapeutically or prophylactically effective amounts of the compounds described herein.

DESCRIPTION OF THE PREFERRED EMBODIMENTS

In one aspect, the present invention involves a compound having the structure where $R^1$ is absent or H; $R^2$ is H, $CH_3$, $C_2H_5$ or $C_3H_7$; $R^3$ is H; $R^4$ and $R^{4a}$ are independently H, $CH_3$, $C_2H_5$ or $C_3H^5$; $R^5$ is H, F or Cl; $R^6$ is H; $R^7$ is F or Cl; $R^8$ is H or $CH_3$; and X is O or NH with the provisos that when $R^2$ is $CH_3$, $R^4$ and $R^{4a}$ are H; and when $R^2$ is H, $R^4$ is $CH_3$. $R^1$ is most preferably absent and the nitrogen uncharged.

Another important aspect of the present invention is the use of the above compound or previously unused kynurenic, indole or pyridine derivatives and the like to inhibit undesired neural spasms or binding of neurologically active agents to the strychnine-insensitive glycine-binding portion of the NMDA receptor.

EXAMPLE 1

Synthesis of Ethyl-4-methylamino-5,7-dichloro-2-quinoline Carboxylate

Ethyl-4-methylamino-5,7-dichloro-2-quinoline carboxylates were synthesized by first reacting 3,5-dichloroaniline with ethylethoxy alkyl acetate (or ethyl ethoxalylacetate) in glacial acetic acid, followed by ring closure in mineral oil at 250° C. The product was then refluxed with 4-toluene sulfonyl isocyanate in anhydrous acetonitrile to give the tosylamino derivative. Alkylation was accomplished by refluxing the tosylamino compound in anhydrous acetonitrile with methyl iodide and sodium carbonate. Removal of the rosylate in 90% sulfuric acid at 0° C. gave ethyl 4-methylamino-5,7-dichloro-2-quinoline carboxylate.

EXAMPLE 2

5,7 Difluoro-quinoline-2-carboxylate

The 5,7-difluoro or analogous derivatives are produced by repeating the above reaction sequence but utilizing 3,5-difluoro or analogous anilines in place of the above 3,5-dichloro-aniline.

EXAMPLE 3

Butyl 4-Methylamino-5,7-dichloro-2-quinoline Carboxylate

The butyl ester was produced by repeating the procedure of Example 1 and then hydrolyzing the ethyl ester to the corresponding carboxylic acid with lithium hydroxide. The dried product of this reaction was then refluxed with thionyl chloride in anhydrous 1-butanol. The butyl ester was isolated from this. Analogous alkyl esters are, of course, analogously produced with other alkyl alcohols. Amides (where X is NH) are produced by substituting primary or secondary amines for the alcohols.

EXAMPLE 4

Alkyl 4-Methylamino-5,7-dichloro-2-quinoline Carboxylates

Other Alkyl 4-methylamino-5,7-dichloro-2-quinoline carboxylates may be generally produced utilizing the procedures in the above examples, particularly the last where other alkyl alcohols such as n-propanol or isopropanol are substituted for n-butanol.

EXAMPLE 5

Other N-alkyl Derivatives

N-alkylation of the tosylamino precursors described in the preceding examples may also be conducted with other halogenated alkanes, to produce other 4-alkyl amino products, e.g., bromoethane to give 4-ethyl amino derivatives.

EXAMPLE 6

Compounds of the present invention having unesterified free 2-carboxylate functions may be synthesized by the above procedures while omitting the thionyl chloride-alcohol step.

EXAMPLE 7

Anticonvulsant Effects of Certain Compounds of the Present Invention

Biological Testing

Compounds were screened for anticonvulsant activity in male Carworth Farms number-1 mice. Test solutions of all compounds were prepared in 30% polyethylene glycol 400, and animals were dosed intraperitoneally at either 30 minutes or 4 hours prior to testing. Testing was conducted on four mice at each of three dose levels (30, 100, and 300 mg/kg).

Maximal electroshock seizures (MES) were elicited with a 60 cycle alternatiing current of 50-mA intensity (five to seven times that necessary to evoke minimal electroshock threshold seizures). Current was delivered via corneal electrodes for 0.2 s. A drop of 0.9% saline was instilled in the eye prior to application of electrodes. Abolition of the hindlimb tonic extension component of the seizure was defined as protection in the MES test.

In the subcutaneous pentylenetetrazole (Metrazol) seizure threshold test(met), 85 mg/kg pentylenetetrazole was administered as a 0.5% solution in the posterior midline. Protection in this test was defined as a failure to observe a single episode of clonic spasms of at least 5 s duration during the 30 minute period following administration of the convulsive agent.

Animals were also tested for neurological deficit using the rotorod. After treatment, the animal was placed on a 1 inch diameter knurled plastic rod rotating at 6 rpm. Neurologic deficit was defined as the failure of the animal to remain on the rod for 1 minute.

The compound ethyl-4-methylamino-5,7-dichloro-2-quinoline carboxylate was tested and found to be a particularly effective anticonvulsant agent. This compound is also described as 5,7-dichloro-4-methylamino-kynurenine-2-ethyl ester in Example 8. The experiment is summarized in the following Table 1.

TABLE 1

4-METHYLAMINO-5, 7-DICHLORO-2-QUINOLINE CARBOXYLATE ETHYLESTER
Test Results
Phase I Identification: Mice, i.p.

ADD NUMBER 202007    CLASS 1
Supplier No. 419     Lot No.________
Date Started 10-23-91
Date Completed 10-24-91
Batch Date 10-17-91
Solvent MC 0.5% (M & P, SB)
Avg. animal wt: 21.8 gm    Reference: Book 221 Page 156
range: 18.5–25.5 gm

| FORM | sus | sus | sus |
|---|---|---|---|
| | HOURS 30 MINUTES | | |
| mg/kg | 30 | 100 | 300 |
| MES | 0/1 | 0/3 | 0/1 |
| Sc MET | 1/1[1] | 1/1[2] | 1/1[3] |
| TOX | 0/4 | 0/8 | 0/4 |
| | 4 HOURS MINUTES | | |
| mg/kg | 30 | 100 | 300 |
| MES | 0/1 | 0/3 | 0/1 |
| Sc MET. | 0/1 | 0/1 | 0/1 |
| TOX | 0/2 | 0/4 | 0/2 |

COMMENTS
[1]Repeated: 1/4 protected, 0/4 toxic.
[2]Repeated: 2/4 protected, 0/4 toxic.
[3]Repeated: 1/4 protected, 0/4 toxic.
0 g 6a The anticonvulsant activity of 4-amino-5,7-dichloro-2-quinoline carboxylate methyl ester is shown in Table 2.

TABLE 2

4-AMINO-5, 7-DICHLORO-2-QUINOLINE
CARBOXYLATE METHYLESTER
Test Results
Phase I Identification: Mice, i.p.

ADD NUMBER 210001     CLASS 1
Supplier No. 419     Lot No.___________
Date Started 06-26 92
Date Completed 06-26-92
Batch Date 06-04-92
Solvent MC 0.5% (M & P, SB)
Avg. animal wt: 19.7 gm     Reference: Book 234 Page 282
range: 18.5–21.5 gm

| FORM | sus | sus | sus |
|---|---|---|---|
| HOURS 30 MINUTES | | | |
| mg/kg | 30 | 100 | 300 |
| MES | 0/1 | 0/3 | 0/1 |
| Sc MET | 0/1 | 1/1 | 0/1 |
| TOX | 0/4 | 0/8 | 0/4 |
| 4 HOURS MINUTES | | | |
| mg/kg | 30 | 100 | 300 |
| MES | 0/1 | 1/3 | 1/1 |
| Sc MET. | 0/1 | 0/1 | 0/1 |
| TOX | 0/2 | 0/4 | 0/2 |

COMMENTS

The anticonvulsant activity of 4-methylamino-5,7-dichloro-2-quinoline carboxylate acid is shown in Table 3.

TABLE 3

4-METHYLAMINO-5, 7-DICHLORO-2-QUINOLINE
CARBOXYLATE ACID
Test Results
Phase I Identification: Mice, i.p.

ADD NUMBER 204068     CLASS 2
Supplier No. 419     Lot No.___________
Date Started 01-08-92
Date Completed 01-08-92
Batch Date 12-12-91
Solvent MC 0.5% (M & P, SB)
Avg. animal wt: 24.5 gm     Reference: Book 221 Page 293
range: 22.0–25.5 gm

| FORM | sus | sus | sus |
|---|---|---|---|
| HOURS 30 MINUTES | | | |
| mg/kg | 30 | 100 | 300 |
| MES | 0/1 | 0/3 | 1/1 |
| Sc MET | 1/2 | 0/1 | 1/1 |
| TOX | 0/4 | 0/8 | 4/4[1] |
| 4 HOURS MINUTES | | | |
| mg/kg | 30 | 100 | 300 |
| MES | 0/1 | 0/3 | 0/1 |
| Sc MET. | 0/1 | 0/1 | 0/1 |
| TOX | 0/2 | 0/4 | 0/2 |

COMMENTS
[1]Unable to hold onto rotorod. 0/2 MES animals dead (300 mg/kg) after 24 hrs.

The lack of anticonvulsive activity for 4-amino-5,7-dichloro-2-quinoline carboxylate acid is shown in Table 4.

TABLE 4

Test Results
4-AMINO-5, 7-DICHLORO-2-QUINOLINE CARBOXYLATE
ACID
Phase I Identification: Mice, i.p.

ADD NUMBER 212002     CLASS 3
Supplier No. 419     Lot No.___________
Date Started 09-09-92
Date Completed 09-09-92
Batch Date 08-20-92
Solvent MC 0.5% (M & P, SB)
Avg. animal wt: 22.4 gm     Reference: Book 238 Page 133
range: 20.0–24.0 gm

| FORM | sus | sus | sus |
|---|---|---|---|
| HOURS 30 MINUTES | | | |
| mg/kg | 30 | 100 | 300 |
| MES | 0/1 | 0/3 | 0/1 |
| Sc MET | 0/1 | 0/1 | 0/1 |
| TOX | 0/4 | 0/8 | 0/4 |
| 4 HOURS MINUTES | | | |
| mg/kg | 30 | 100 | 300 |
| MES | 0/1 | 0/3 | 0/1 |
| Sc MET. | 0/1 | 0/1 | 0/1 |
| TOX | 0/2 | 0/4 | 0/2 |

COMMENTS
0.124 g

The lack of anticonvulsant activity for 4-methylamino-5, 7-dichloro quinoline 2-carboxylate methyl ester is shown in Table 5

TABLE 5

4-METHYLAMINO-5, 7-DICHLORO-2-QUINOLINE
CARBOXYLATE METHYLESTER
Test Results
Phase I Identification: Mice, i.p.

ADD NUMBER 207061     CLASS 3
Supplier No. 419     Lot No.___________
Date Started 04-20-92
Date Completed 04-20-92
Batch Date 03-05-92
Solvent MC 0.5% (M & P, SB)
Avg. animal wt: 23.0 gm     Reference: Book 234 Page 9
range: 20.5–24.5 gm

| FORM | sus | sus | sus |
|---|---|---|---|
| HOURS 30 MINUTES | | | |
| mg/kg | 30 | 100 | 300 |
| MES | 0/1 | 0/3 | 0/1 |
| Sc MET | 0/1 | 0/1 | 0/1 |
| TOX | 0/4 | 0/8 | 0/4 |
| 4 HOURS MINUTES | | | |
| mg/kg | 30 | 100 | 300 |
| MES | 0/1 | 0/3 | 0/1 |
| Sc MET. | 0/1 | 0/1 | 0/1 |
| TOX | 0/2 | 0/4 | 0/2 |

COMMENTS
0.416 g

The lack of anticonvulsant activity of ester-4-methylamino-5,7-dichloro quinoline-2-carboxylate n-butyryl is seen in Table 6.

TABLE 6

4-METHYLAMINO-5, 7-DICHLORO-2-QUINOLINE-2-CARBOXYLATE n-BUTYRYLESTER
Test Results
Phase I Identification: Mice, i.p.

ADD NUMBER 210061     CLASS 31
Supplier No. 419     Lot No.______
Date Started 07-16-92
Date Completed 07-16-92
Batch Date 06-11-92
Solvent MC 0.5% (M & P, SB)
Avg. animal wt: 23.6 gm     Reference: Book 238 Page 47
range: 22.0–25.5 gm

| FORM | sus | sus | sus |
|---|---|---|---|
| HOURS 30 MINUTES | | | |
| mg/kg | 30 | 100 | 300 |
| MES | 0/1 | 0/3 | 0/1 |
| Sc MET | 0/1 | 0/1 | 0/1 |
| TOX | 0/4 | 0/8 | 0/4 |
| 4 HOURS MINUTES | | | |
| mg/kg | 30 | 100 | 300 |
| MES | 0/1 | 0/3 | 0/1 |
| Sc MET. | 0/1 | 0/1 | 0/1 |
| TOX | 0/2 | 0/4 | 0/2 |

COMMENTS
0.352 g

While the methyl and butyl esters were inactive, it is believed, in view of the ethyl ester activity, that the propyl ester (n or i) will have anticonvulsive activity.

EXAMPLE 8

Syntheses—All chemicals for synthetic procedures were obtained from Aldrich. The 7-chloro-, bromo-, and iodo-derivatives of kynurenic acid were synthesized as reported by Surrey and Hammer (1946). Other derivatives were prepared in a similar manner. Briefly, the substituted aniline was reacted with ethyl ethoxalylacetate, followed by ring closure in mineral oil at 250° C. This yielded the substituted kynurenate ethyl ester (5-, 6-, 7-, and/or 8-substituted ethyl 4-hydroxy-2-quinoline carboxylate). In those cases where ring closure could result in the production of isomeric forms of the ester, structural configuration was determined using nuclear magnetic resonance. Basic hydrolysis of the ester provided the corresponding substituted acid. To replace the hydroxyl with the amino moiety at the 4-position, a tosylimino derivative was formed by reacting 5,7-dichloro-kynurenate ethyl ester with 4-toluenesulphonyl isocyanate (Wright, 1984). Alkylation of the tosylimino derivative with methyl iodide, followed by detosylation in sulfuric acid afforded the corresponding 4-methylamino compound. Hydrolysis with lithium hydroxide gave 5,7-dichloro-4-methylamino-kynurenic acid. The procedure of Harrison et al. (1990) was also used to make methyl 5,7-dichloro-kynurenate carboxylate which then served as the precursor for 4-methylamino-5,7-dichloro-2-quinoline carboxylic acid. In this method, dimethyl acetylenedicarboxylate is used in place of ethyl ethoxalylacetate to form the quinoline ring system.

Indole and pyridine esters were prepared by treating the respective acids with thionyl chloride, and refluxing the resulting acid chlorides with the appropriate alcohols.

Structures were verified using nuclear magnetic resonance spectroscopy, mass spectroscopy, and/or elemental analysis.

Biological testing—Compounds were screened for anticonvulsant activity in male Carworth Farms number-one mice. Test solutions of all compounds were prepared in 30% polyethylene glycol 400, and animals were dosed intraperitoneally at either 30 min or 4 h prior to testing. Testing was conducted on four mice at each of three dose levels (30, 100, and 300 mg/kg).

Maximal electroshock seizures (MES) were elicited with a 60 cycle alternating current of 50-mA intensity (five to seven times that necessary to evoke minimal electroshock threshold seizures). Current was delivered via corneal electrodes for 0.2 s. A drop of 0.9% saline was instilled in the eye prior to application of electrodes. Abolition of the hindlimb tonic extension component of the seizure was defined as protection in the MES test.

In the subcutaneous pentylenetetrazole (Metrazol) seizure threshold test (Met), 85 mg/kg pentylenetetrazole was administered as a 0.5% solution in the posterior midline. Protection in this test was defined as a failure to observe a single episode of clonic spasms of at least 5 s duration during the 30 min period following administration of the convulsive agent.

Animals were also tested for neurological deficit using the rotorod. After treatment, the animal was placed on a 1 inch diameter knurled plastic rod rotating at 6 rpm. Neurologic deficit was defined as the failure of the animal to remain on the rod for 1 min.

Binding Studies—Inhibition of [$^3$H]glycine specific binding was assayed using [$^3$H]glycine (43 Ci/mmol) obtained from DuPont-New England Nuclear. Inhibition was determined for each compound in "buffy coat" membranes as described by Jones et al. (1989). Membranes were prepared from rat cerebral cortex and assays were conducted in Na-free 50 mM HEPES (Sigma) at pH 7.4. Membranes were incubated in a final volume of 1 ml with 20 nM [$^3$H]glycine and a 10 uM concentration of the test compound. Although experience has shown that [$^3$H]glycine binding in this preparation is strychnine insensitive, 10 uM strychnine was added to the assay mixtures to eliminate the possibility that any effects studied could be mediated through a strychnine-sensitive process. Incubation was continued for 20 min at 4° C. Non-specific binding was determined in the presence of 1 mM glycine and subtracted. All conditions were tested in triplicate in 3 different assays. Binding was terminated using a Brandel M-24C cell harvester employing rapid filtration through GF/C glass fiber filters pre-soaked in 1% (V/V) polyethylenimine. Filters were washed twice with 5 ml buffer cooled to 4° C. Radioactivity bound to the filters was determined with a Beckman LS-5000TD liquid scintillation counter. Results were corrected for non-specific binding and expressed as relative inhibition of [$^3$H]glycine binding by comparison of the test compound to standard inhibition by 10 uM 7-Cl-2-kynurenate (Inhibition by standard/inhibition by test compound). The standard 7-Cl-2-kynurenate displays an $IC_{50}$ for glycine binding in this test system of 0.27–0.56 uM (Foster, et al., 1992; Kemp, et al., 1988; Snell, 1990).

Figure 1:
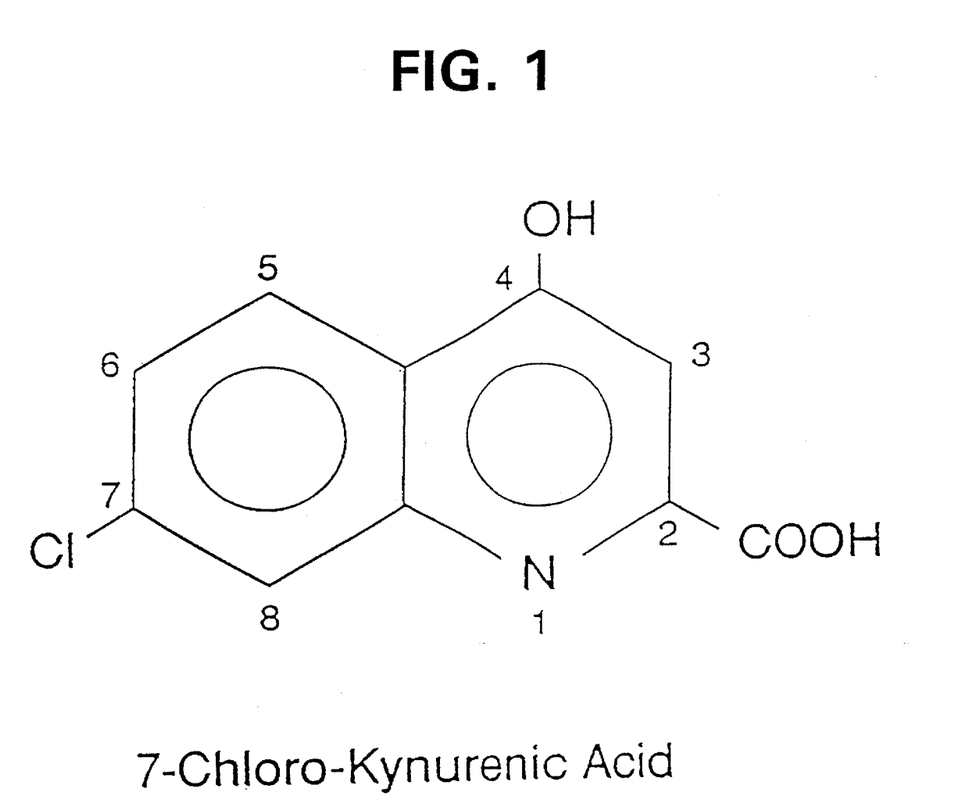
FIG. 1, for illustrative purposes, shows the structure of 7-chloro-kynurenic acid.

Twenty-five kynurenic acid derivatives were synthesized with various substitutions in the 4, 5, 6, 7, and 3 positions (FIG. 1). Both acid and ester derivatives were tested to determine what effect replacement of the ionizable acid group at the 2-position had on potency. Each compound was tested for anticonvulsant activity and inhibition of strychnine-insensitive [$^3$H]glycine binding.

Figure 2:
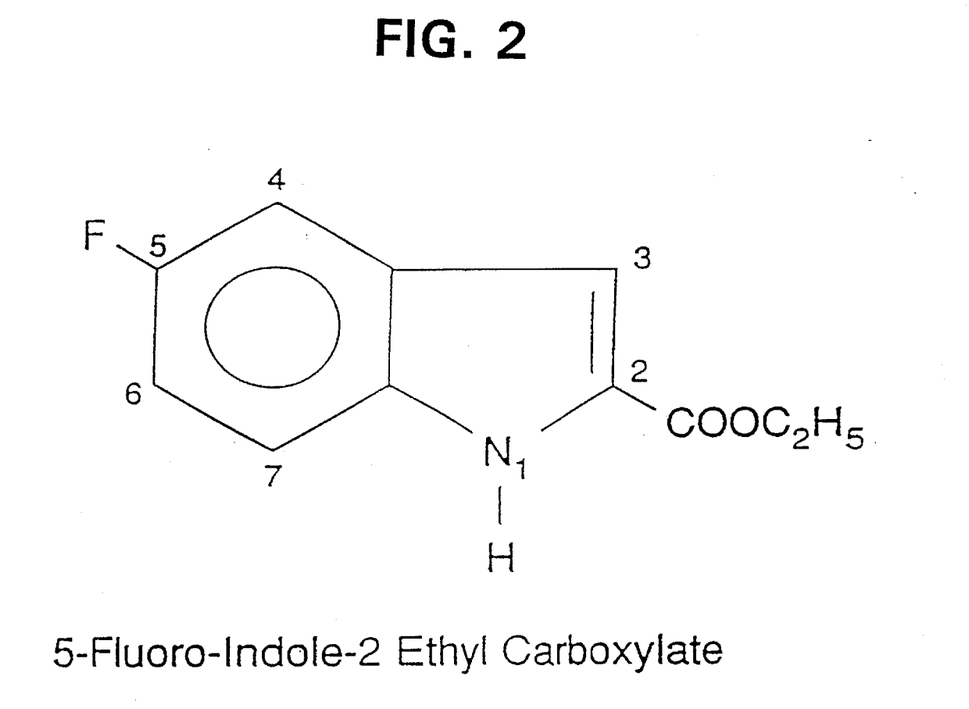
FIG. 2, for illustrative purposes shows the structure of 5-fluoro-indole-2-ethyl carboxylate.
Figure 3:
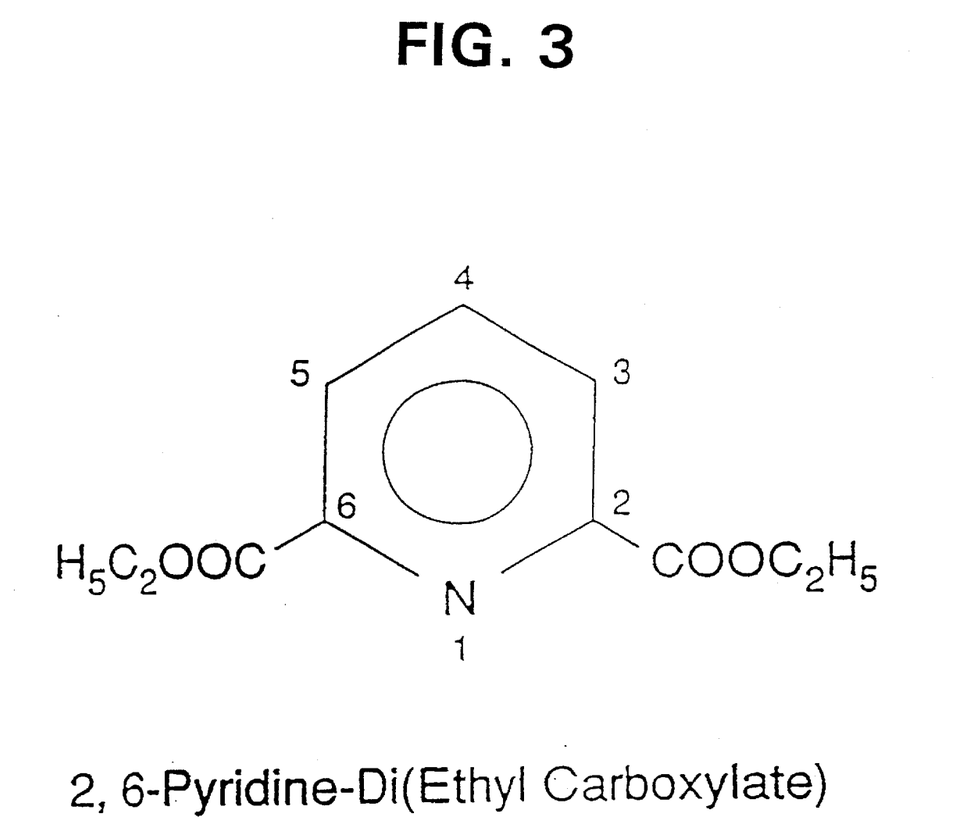
FIG. 3, for illustrative purposes, shows the structure of 2,6-pyridine-di(ethyl carboxylate).

The ethyl esters of five different 5-substituted indole-2-carboxylic acids (FIG. 2) were made along with the butyl ester of 5-fluoro-indole-2-carboxylic acid. The diethyl ester of 2,6-pyridine-dicarboxylic acid was also synthesized (FIG. 3). Again both the acid and ester forms were tested for anticonvulsant activity and [$^3$H]glycine inhibition.

Six of the twenty-five kynurenic acid derivatives had anticonvulsant activity (Table 7), and each of these showed glycine displacement (Table 8).

TABLE 7

Compounds Active in Anticonvulsant Testing[a]

| Compound | Effective or (Maximum Ineffective) Intraperitoneal Dose (mg/kg) | | |
|---|---|---|---|
| | MES | Met | Rotored |
| 5,7-di-Cl-4-methylamino-kyn-2-ethyl ester | (300) | 30 | (300) |
| 5-F-indole-2-COOH | 100 | (300) | (300) |
| 5,7-di-F-kyn-2-ethyl ester | 300 | (300) | (300) |
| 5,7-di-Cl-4-methylamino-kyn-2-COOH | 100 | 300 | 100 |
| 5-F-indole-2-ethyl ester | 100 | 300 | (300) |
| 5-methoxy-indole-2-ethyl ester | 300 | 100 | 300 |
| 2,6-pyridine-di-(ethyl carboxylate) | (300) | 100 | 300 |
| 5-Cl-indole-2-COOH | (300) | 100 | 300 |
| 5-F-indole-2-butyl ester | (300) | 300 | (300) |
| 7-Cl-kyn-2-ethyl ester | (300) | 300 | (300) |
| 5,7-di-Cl-kyn-2-COOH | (300) | 300 | (300) |
| 7-Cl-8-methyl-kyn-2-COOH | (300) | 300 | (300) |
| 5-methoxy-indole-2-COOH | (300) | (300) | 300 |
| 2,6-pyridine dicarboxylic acid | (300) | (300) | 300 |

[a]Experimental details are presented in the text.

TABLE 8

Inhibition of Binding of [$^3$H] Glycine (20 nM) by Kynurenate, Indole, and Pyridine Derivatives at 10 uM: Relative Effectiveness Compared with the Standard Inhibitor, 7-Cl-2-Kynurenic acid: (7-Cl-Kyn)

| | Relative Inhibition[a] |
|---|---|
| Kynurenate Derivative (10 uM) | |
| 7-Cl-Kyn | 1.00 |
| 5,7-di-Cl-4-methylamino-2-COOH | 1.32 ± 0.19 |
| 5,7-di-F-2-COOH | 1.01 ± 0.04 |
| 7-Cl-2-ethyl ester[b] | 0.95 ± 0.15 |
| 5,7-di-Cl-2-COOH | 0.90 ± 0.06 |
| 5,7 0-di-Cl-2-ethyl ester | 0.90 ± 0.19 |
| 5,7-di-Cl-4-methylamino-2-methyl ester | 0.89 ± 0.03 |
| 6-CH$_3$-7-Cl-2-COOH | 0.82 ± 0.11 |
| 7-F-2-COOH | 0.78 ± 0.06 |
| 2-Br-2-COOH | 0.74 ± 0.05 |
| 5,7-di-Cl-4-amino-2-COOH | 0.73 ± 0.12 |
| 7-I-2-COOH | 0.69 ± 0.06 |
| 7-F-2-ethyl ester | 0.66 ± 0.13 |
| 7-Cl-8-CH$_3$-2-COOH | 0.66 ± 0.14 |
| 5,7-di-Cl-4-methylamino-2-ethyl ester | 0.65 ± 0.09 |
| 5,7-di-Cl-4-methylamino-2-butyl ester | 0.61 ± 0.09 |
| 5,7-di-F-2-ethyl ester | 0.59 ± 0.04 |
| 5,8-di-Br-2-ethyl ester | NA[c] |
| 6,7-di-Cl-2-ethyl ester | NA |
| 6,7-di-Cl-2-COOH | NA |
| 6-methyl-7-Cl-2-ethyl ester | NA |
| 6-F-7-Cl-2-ethyl ester | NA |
| 7-Br-2-ethyl ester | NA |
| 7-I-2-ethyl ester | NA |
| 7-Cl-8-methyl-2-ethyl ester | NA |
| Indole Derivative | |
| 5-F-2-COOH | 0.87 ± 0.04 |
| 5-methoxy-2-COOH | 0.83 ± 0.07 |
| 5-Cl-2-COOH | 0.71 ± 0.08 |
| 5-F-2-ethyl ester | 0.67 ± 0.08 |
| 5-F-2-butyl ester | 0.63 ± 0.10 |
| 5-hydroxyl-2-ethyl ester | 0.44 ± 0.63 |
| 5-methoxy-2-ethyl ester | NA |
| 5-Cl-2-ethyl ester | NA |
| 2-ethyl ester | NA |
| Pyridine Derivative | |
| 2,6-di-(ethyl carboxylate) | 0.89 ± 0.10 |
| 2,6-dicarboxylic acid | NA |

[a]Each value is the mean ± S.E.M. of 3 to 6 determinations, each performed in triplicate
[b]2-COOCH$_2$CH$_3$
[c]Not active Experimental details are presented in the text.

The most potent anticonvulsant was the ethyl ester of 5,7-dichloro-4-methylamino-kyn (ethyl 4-methylamino-5,7-dichloro-2-quinoline carboxylate) which was active in the MET test at a dose of 30 mg/kg. The carboxylic acid form of this compound was the best inhibitor of [$^3$H]glycine binding, although it was less potent as an anticonvulsant agent (100 mg/kg in the MES test). This was the only kynurenate which caused a neurological deficit in the rotorod test (at 300 mg/kg). The ethyl ester of 7-chloro-kyn, along with the acid forms of 5,7-dichloro-kyn and 7-chloro-8-methyl-kyn were active in the Met test (300 mg/kg). The ethyl ester of 5,7-difluoro-kyn was effective in the MES test (300 mg/kg). Eleven other kynurenic acid derivatives displaced [$^3$H]glycine in the binding assay but had no measured in vivo activity. Poor solubility is characteristic of these compounds, hence they may not reach effective concentrations in the CNS.

As a group, the indole-2-carboxylic acid derivatives were more potent anticonvulsant agents than the kynurenates (Table 7), although their inhibition of glycine binding was not markedly different (Table 8). Substitution of a fluorine at the 5-position on the indole ring system produced compounds which gave good glycine binding inhibition in both the acid and ester forms. The 5-fluoro derivatives also had anticonvulsant action. Both 5-fluoro-indole-2-carboxylic acid and its ethyl ester had MES activity at 100 mg/kg. However, the butyl ester was active only at a dose level of 300 mg/kg, although its binding characteristics were similar to those of the ethyl ester. Replacement of the fluorine with a chlorine atom produced a compound which, in the acid form, provided Met protection at 100 mg/kg, but caused a neurological deficit on the rotorod at 300 mg/kg. Although the acid form of the chloro derivative displayed binding competition similar to that seen with the 5-fluoro derivative, the ethyl ester was inactive in both glycine inhibition and in vivo testing. Placement of a methoxy group at the 5-position on the indole ring system produced a compound with glycine binding inhibition but no anticonvulsant activity. However, the ester form had Met activity at 100 mg/kg and MES protection at 300 mg/kg. It also produced a neurological deficit at 300 mg/kg. This compound (5-methoxy-indole-2-ethyl carboxylate) was unusual in that it was the only chemical tested which demonstrated anticonvulsant activity, but did not compete for [$^3$H]glycine binding. The 5-hydroxyl-2-ethyl carboxylate derivative was the only compound in this group which had binding activity, but no CNS effects.

Despite having a configurational similarity to the nitrogen containing ring of the 2-carboxy quinolines, pyridine-2,6-dicarboxylic acid showed no glycine displacement (Table 8). However, the diethyl ester had anticonvulsant activity at 100 mg/kg (Met) and potent [$^3$H]glycine displacement. Both compounds caused a neurological deficit in the rotorod test at 300 mg/kg.

Of the twenty-five kynurenates which were synthesized, seventeen showed competition for [$^3$H]glycine binding to cortical membranes. Six of these had anticonvulsant activity as tested in vivo. Both 5,7-dichloro-4-methylamino-kyn and its ethyl ester, were active at dose levels of 100 mg/kg or less. It has been reported that in aqueous solution at pH 7, 4-hydroxy-quinolines such as kynurenic acid exist predominantly as the 4(1H)-quinolone tautomer (Tucker and Irvin, 1951), and that this may be a preferred form for receptor binding (Huettner, 1991). Harrison et al. (1990) have suggested that the greater binding potency of the 4-amino-kyn derivatives is due to the ease with which they tautomerize. The fact that the ethyl ester had high anticonvulsant activity but poor binding inhibition may reflect better solubility properties. All of the kynurenate derivatives were poorly soluble in aqueous solutions at pH 7. However, this ester was the only derivative that was appreciably soluble in chloroform and other non-polar solvents. Thus, the in vivo activity found with the ester may reflect crossing of the blood-brain barrier in sufficient concentration to be effective, despite a comparatively low affinity for glycine binding. The argument also can be made that while the acid forms of the 4-amino derivatives interact primarily with the glycine site (Foster et al., 1992), the ethyl ester may manifest its anticonvulsant effects through some other set of receptors. Methyl and n-butyl esters of 5,7-dichloro-4-methylamino-kyn were inactive in anticonvulsant testing.

Baron et al. (1990) reported the ability of intracerebroventricularly administered 5,7-dichloro-kyn to protect against quinolinic acid induced seizures in CD-1 mice and against sound induced seizures in DBA/2J mice. Herein is described activity of this compound against Met seizures at following intraperitoneal administration at 300 mg/kg. Although the ester form was inactive, the ethyl ester of a similar compound, 5,7-difluoro-kyn, had MES activity at this dose level. Of the six kyn derivatives with anticonvulsant activity, three were esters and three were ionizable acids. It has been reported by McBain et al. (1989) that an ionized carboxyl group is essential for agonist activity at the NMDA-associated glycine site. The present results show that esterification of the acid does not eliminate antagonist binding at that site, although it may decrease affinity. Three of the kynurenates had only Met activity, two had only MES activity, and one had both. Each of the six showed inhibition of [$^3$H]glycine binding. Antagonist potency has previously been associated only with derivatives having electronegative substituents on the benzene ring (Huettner, 1991). It should also be noted that the 6-methyl-7-chloro-kyn displayed glycine-binding inhibition, but no anticonvulsant activity. Of the eight kynurenates that showed no glycine-binding inhibition, seven were esters. Lack of induced neurological deficit, as determined by the rotorod test, was a distinguishing characteristic of the kynurenates.

Five of nine indole-2-carboxylic derivatives had anticonvulsant activity, and four of these were active at the 100 mg/kg dose level. Huettner (1989) reported that electron withdrawing substituents at the 5-position on the indole ring enhanced glycine binding, while electron releasing groups lowered binding affinity. With one exception this also held true for anticonvulsant activity. The most potent inhibitor of [$^3$H]glycine binding in this group was 5-fluoro-indole-2-carboxylic acid. It was also a good anticonvulsant with MES activity at 100 mg/kg. The ethyl ester form of this compound had MES activity at 100 mg/kg and Met activity a, 300 mg/kg. The butyl ester provided Met protection at 300 mg/kg. None of these derivatives demonstrated neurological deficit in rotorod testing. Replacement of the fluorine atom with a 5-chloro abolished activity for the ester. Met protection was also seen with the 5-chloro-indole-2-carboxylic acid, but it produced a neurological deficit at 300 mg/kg. The compound 5-methoxy-indole-2-ethyl carboxylate was the only derivative tested which had anticonvulsant activity but did not inhibit [$^3$H]glycine binding. It had Met activity at 100 mg/kg and MES protection at 300 mg/kg. When the methoxy moiety is placed on an aromatic ring it serves as an electron releasing group, so a loss of glycine binding was predicted. However, the unexpected anticonvulsant activity must be the result of some mechanism other than inhibition of glycine binding at the NMDA receptor. Given the anticonvulsant potential of this group of compounds, it should be possible to produce derivatives having sufficient activity (in the 30 mg/kg dose range) for therapeutic use.

The diethyl ester of pyridine-2,6-dicarboxylic acid inhibited glycine binding and had anticonvulsant activity while the parent acid did neither in the present tests. That the acid form did cross the blood-brain barrier is evidenced by the rotorod test. Ring substitution on the pyridine ester should improve the activity of that compound. As the ester showed glycine binding inhibition and the dicarboxylic acid did not, other ester or amide derivatives are worth further investigation.

Chemicals which show activity in the MES test are classified as preventing seizure spread, while those effective against Met induced seizures are described as altering seizure threshold (Swinyard and Kupferberg, 1985) while both are viewed as inhibiting convulsions. However, these classifications do not address what is actually occurring on the cellular level. Effective anticonvulsant agents often are active in both tests, and minor structural modifications may enhance potency in one test system relative to the other. For example, diphenylhydantoin (Dilantin) is an anticonvulsant drug with potent MES activity. Maximal MES activity is seen when the hydantoin ring has two phenyl groups substituted at carbon 5. However, replacement of one phenyl group with an ethyl group imparts moderate Met activity to the molecule with only a slight decrease in the MES activity (Vida and Gerry, 1977). If the ethyl group is then replaced with a hydrogen, MES activity is decreased even more, while MET effectiveness is enhanced (Cortes et al., 1985). Similar findings were seen with the compounds of the present invention, in that small structural modifications which had little apparent impact on binding inhibition could dramatically alter the outcome of anticonvulsant testing. The acid form of 5,7-dichloro-kyn had mild Met activity. Substitution of the methylamino for the hydroxyl at the 4-position did not alter Met effects but imparted moderate MES activity to the molecule. Esterification of this compound abolished Met protection but maximized MES activity. While these structure-activity comparisons demonstrate that small structural modifications do affect anticonvulsant responses, they do not address what effect this has on mechanism of action. Such changes may increase binding affinity for another type of receptor, or, by altering solubility properties, allow the derivative to interact with similar receptors in synapses largely inaccessible to the parent compound. Both of these cases would result in a different set of neuronal pathways being activated or inhibited. Another possibility is that both compounds bind the same receptor, but the effects of binding differ with each compound.

The parent compound, kynurenic acid, is a nonselective excitatory amino acid antagonist having activity at NMDA, quisqualate, and kainate receptors. However, the 7-Cl derivative is much more specific with a high affinity for the strychnine-insensitive glycine binding site relative to glutamate sites ($IC_{50}$=0.56 uM for glycine, $IC_{50}$=169 uM for NMDA, $IC_{50}$=153 uM for quisqualate, and $IC_{50}$>1000 for kainate) (see also Kemp, et al., 1988). It can be argued that the differences between MES and Met anticonvulsant activities reflect ligand interactions at different excitatory receptors. Of the eleven compounds which demonstrated both anticonvulsant activity and glycine binding inhibition, eight were active against pentalenetetrazole induced seizures. However, one of the three compounds having only MES activity, 5-F-indole-2-COOH, has been shown to inhibit competitively the potentiating action of glycine on current elicited by NMDA in whole cells (Huettner, 1989). While this demonstrates that the compound is a ligand for in vivo glycine binding, it does not necessarily mean that the observed anticonvulsant activity is a manifestation of this binding. In voltage-clamped Xenopus oocytes injected with rat brain mRNA, 7-Cl-kyn was approximately 40-fold more potent as an antagonist at the NMDA-associated glycine site than at the receptor mediating kainate currents (Kleckner and Dingledine, 1989). Other substitutions on the kynurenate ring system could potentiate kainate binding relative to that at the glycine site. Since the anticonvulsant tests themselves have not been associated with specific dysfunctions in either neural pathways or receptor-ligand interactions, it is difficult to determine what protection against MES or Met induced seizures signifies at the molecular level. However, an examination of the binding affinities of the active compounds for other receptor sites should help clarify these structure-activity relationships.

While the role of the NMDA receptor-complex in epilepsy is still not well understood, the present invention involves a showing that compounds which inhibit glycine binding to this complex can have potent anticonvulsant activity. The fact that this activity was seen following systemic administration, argues that these types of chemicals have therapeutic potential.

The following citations are incorporated in pertinent part by reference herein for the reasons cited in the above text.

REFERENCES

Baron et al. (1990) Activity of 5,7-dichlorokynurenic acid, a potent antagonist at the N-methyl-D-aspartate receptor-associated glycine binding site. *Mol. Pharmacol.* 38, 554–561.

Collingridge, et al. *TINS,* 10 (1987) pp. 288–293.

Cortes et al. (1985) Effect of structural modification of the hydantoin ring on anticonvulsant activity. *J. Med. Chem.* 28, 601–606.

Dingledine et al. (1990) Excitatory amino acid receptors in epilepsy. *Trends Pharmacol. Sci.* 11, 334–338.

Foster et al. (1992) Kynurenic acid analogues with improved affinity and selectivity for the glycine site on the N-methyl-D-asparate receptor from rat brain. *Mol. Pharmacol.* 41, 914–922.

Foster, *Adv. Neurol.,* 51 (1990) pp. 97–102.

Giulian, et al. *Science,* 250 (1990) pp. 1593–1596.

Goehring et al. (1990) Synthesis and anticonvulsant activity of 2-benzylglutarimides. *J. Med, Chem.* 33, 926–931.

Greenamyre, et al. *Neurobiol. Aging,* 10 (1989) pp. 593–602.

Harrison et al. (1990) 4-[(Carboxymethyl)oxy]- and 4-[(carboxymethyl)amino]-5,7-dichloroquinoline-2-carboxylic acid: new antagonists of the strychnine-insensitive glycine binding site on the N-methyl-D-aspartate receptor complex. *J. Med. Chem.* 33, 3130–3132.

Huettner (1989) Indole-2-carboxylic acid: a competitive antagonist of potentiation by glycine at the NMDA receptor. *Science* 24, 1611–1613.

Huettner (1991) Competitive antagonism of glycine at the N-methyl-D-aspartate receptor. *Biochem. Pharmacol.* 41, 9–16.

Izumi, et al. *Neurosci. Lett.,* 83 (1987) pp. 201–206.

Johnson et al. (1987) Glycine potentiates the NMDA response in cultured mouse brain neurons. *Nature* 325, 529–531.

Johnson, et al. *Nature,* 325 1987) pp. 529–531.

Jones et al. (1989) Characterization of the binding of radioligands to the N-methyl-D-asparate, phencyclidine, and glycine receptors in buffy coat membranes. *J. Pharmacol. Methods* 21, 161–168.

Kemp et al. (1988) 7-Chlorokynurenic acid is a selective antagonist at the glycine modulatory site of the N-methyl-D-aspartate receptor complex. *Proc. Natl. Acad. Sci. USA* 85, 6547–6550.

Kleckner et al. (1989) Selectivity of quinoxalines and kynurenines as antagonists of the glycine site on N-methyl-D-aspartate receptors. *Mol. Pharmacol.* 36, 430–436.

McBain et al. (1989) Structural requirements for activation of the glycine coagonist site of N-methyl-D-aspartate receptors expressed in Xenopus oocytes. *Mol. Pharmacol.* 36, 556–565.

Morris, et al. *Nature,* 319 (1986) pp. 774–776.

Nowak et al. (1984) Magnesium gates glutamate-activated channels in mouse central neurones. *Nature* 307, 462–465.

Penney, et al. *J. Neurology, Neurosurgery and Psychiatry,* 53 (1990) pp. 314–320.

Porter et al. (1984) Antiepileptic drug development program. *Cleve. Clin. Q.* 51, 293–305.

Rogawski et al. (1990) Antiepileptic drugs: pharmacological mechanisms and clinical efficacy with consideration of promising developmental stage compounds. *Pharmacol. Rev.* 42, 223–286.

Rondouin, et al. *Neurosci. Lett.,* 91 (1988) pp. 199–202.

Rothman, *J. Neurosci.,* 4 (1984) pp. 1884–1891.

Singh et al. (1990) Modulation of seizure susceptibility in the mouse by the strychnine-insensitive glycine recognition site of the NMDA receptor/ion channel complex. *Br. J. Pharmacol.* 99, 285–288.

Snell (1990). The allosteric interactions between the N-methyl-D-aspartate (NMDA) and glycine sites of the NMDA receptor/ionophore complex. A Dissertation. The University of Texas Medical Branch, Galveston, Tex.

Snell et al. (1986) Characterization of the inhibition of excitatory amino acid-induced neurotransmitter release in the rat striatum by phencyclidine-like drugs. *J. Pharmacol. Exp. Ther.* 238, 938–946.

Spencer, et al. *Science,* 237 (1987) pp. 517–522.

Stone et al. (1981) Quinolinic acid: a potent endogenous excitant at amino acid receptors in CNS. *Eur. J. Pharmacol,* 72, 411–412.

Surrey et al. (1946) some 7-substituted 4-aminoquinoline derivatives. *J. Am. Chem. Soc.* 68, 113–116.

Swinyard et al. (1985) Antiepileptic drugs: detection, quantification, and evaluation. *Federation Proc.* 44, 2629–2633.

Tucker et al. (1951) Apparent ionization exponents of 4-hydroxyquinoline, 4-methoxyquinoline and N-methyl-4-quinoline; evaluation of lactam-lactam tautomerism. *J. Am. Chem. Soc.* 73, 1923–1928.

Vida et al. (1977) *Anticonvulsants.* pp. 176–182, Academic Press, New York, N.Y.

Watkins et al. (1990) Structure-activity relationships in the development of excitatory amino acid receptor agonists and competitive antagonists. *Trends Pharmacol Sci.* 11, 25–33.

White et al. (1989) Glycine binding to rat cortex and spinal cord: binding characteristics and pharmacology reveal distinct populations of sites. *J. Neurochem.* 53, 503–512.

Wong et al. (1986) The anticonvulsant MK-801 is a potent N-methyl-D-asparate antagonist. *Proc. Natl. Acad. Sci. USA* 83, 7104–7108.

Wong, et al. *Proc. Natl. Acad. Sci. USA*, 83 (1986) pp. 7104–7108.

Wright (1984) A simple one-pot conversion of alkyl 4-oxo-1,4-dihydroquinoline-2-carboxylates to 4-aminoquinoline-2-carboxylates using reactive isocyanates. *Synthesis*, 1058–1061.

Young, et al. *Science*, 241 (1988) pp. 981–983.

It is understood that those of skill in the art will understand how to make obvious variations upon the formulae and procedures described in the following claims without departing from the spirit and scope of these claims. For example, pharmaceutically acceptable salts of acidic or basic funtions may be formed and routinely utilized.

What is claimed is:

1. An anticonvulsive compound having the structure:

where:

$R^1$ is absent;

$R^2$ is $C_2H_5$;

$R^3$ is H;

$R^4$ is $CH_3$;

$R^{4a}$ is H;

$R^5$ is Cl;

$R^6$ is H;

$R^7$ is Cl;

$R^8$ is H; and

X is O.

2. A compound having the structure:

where:

$R^1$ is absent;

$R^2$ is H;

$R^3$ is H;

$R^4$ is $CH_3$;

$R^{4a}$ is H;

$R^5$ is Cl;

$R^6$ is H;

$R^7$ is Cl;

$R^8$ is H; and

X is O.

* * * * *

UNITED STATES PATENT AND TRADEMARK OFFICE
CERTIFICATE OF CORRECTION

PATENT NO.: 5,493,027

DATED : February 20, 1996

INVENTOR(S): Alfred C. Nichols, Lemone Yielding

It is certified that error appears in the above-identified patent and that said Letters Patent is hereby corrected as shown below:

Title page, item [75], line 1, replace "San Jose" with --Texas City--

Signed and Sealed this

Twenty-first Day of May, 1996

Attest:

BRUCE LEHMAN

*Attesting Officer*  *Commissioner of Patents and Trademarks*